(12) United States Patent
Ou Yang

(10) Patent No.: US 11,419,959 B2
(45) Date of Patent: Aug. 23, 2022

(54) PORTABLE ULTRAVIOLET STERILIZATION CONTAINER

(71) Applicant: SHENZHEN UVLED OPTICAL TECHNOLOGY CO., LTD., Shenzhen (CN)

(72) Inventor: Chenyi Ou Yang, Yongzhou (CN)

(73) Assignee: SHENZHEN UVLED OPTICAL TECHNOLOGY CO., LTD., Shenzhen (CN)

(*) Notice: Subject to any disclaimer, the term of this patent is extended or adjusted under 35 U.S.C. 154(b) by 462 days.

(21) Appl. No.: 16/477,033

(22) PCT Filed: Apr. 29, 2019

(86) PCT No.: PCT/CN2019/085040
§ 371 (c)(1),
(2) Date: Jul. 10, 2019

(87) PCT Pub. No.: WO2020/206764
PCT Pub. Date: Oct. 15, 2020

(65) Prior Publication Data
US 2021/0330847 A1  Oct. 28, 2021

(30) Foreign Application Priority Data

Apr. 11, 2019 (CN) .......................... 201910290976.X
Apr. 11, 2019 (CN) .......................... 201920489409.2

(51) Int. Cl.
*A61L 2/10* (2006.01)
*A61L 2/26* (2006.01)
*A61L 2/06* (2006.01)

(52) U.S. Cl.
CPC .................. *A61L 2/26* (2013.01); *A61L 2/06* (2013.01); *A61L 2/10* (2013.01); *A61L 2202/11* (2013.01); *A61L 2202/122* (2013.01)

(58) Field of Classification Search
CPC .......... A61L 2/26; A61L 2/10; A61L 2202/11; A61L 2202/122; A61L 2/06
See application file for complete search history.

(56) References Cited

U.S. PATENT DOCUMENTS 10,994,034 B1 * 5/2021 Leavitt ............... B01D 46/0005
2018/0361001 A1 * 12/2018 Liao ........................ A61L 2/24
(Continued)

FOREIGN PATENT DOCUMENTS

CN          208464720 U  *  2/2019
KR      20210109754 A  *  2/2020 ............... A61L 2/10

*Primary Examiner* — Wyatt A Stoffa
(74) *Attorney, Agent, or Firm* — Li & Cai Intellectual Property (USA) Office

(57) ABSTRACT

The invention discloses a portable ultraviolet sterilization container, which comprises a sterilization container body, the sterilization container body has an article storage cavity and a cover, and the sterilization container body is further provided with an illumination device, a heating air duct and a control system. The control system is electrically connected to the illumination device and the heating air duct for controlling the illumination device and the heating air duct to release ultraviolet light and hot air to the article storage cavity, wherein the illumination device comprises a plurality of light-emitting devices which are fixed to a plurality of cavity walls of the article storage cavity. The inner circulation of the heating air duct is from the article storage cavity, through the interior of the cavity wall of the article storage cavity, and then to the article storage cavity.

9 Claims, 4 Drawing Sheets

(56) References Cited

U.S. PATENT DOCUMENTS

| | | | |
|---|---|---|---|
| 2019/0299260 A1* | 10/2019 | Shatalov | A61L 2/24 |
| 2021/0228752 A1* | 7/2021 | Chang | A61L 2/06 |

* cited by examiner

PORTABLE ULTRAVIOLET STERILIZATION CONTAINER

BACKGROUND

1. Technical Field

The present invention relates to a sterilization container, and more particularly to a portable ultraviolet sterilization container.

2. Description of Related Art

Ultraviolet light has a good bactericidal effect and is widely used in the field of sterilization. UV sterilization containers are one of the main applications of UV light in the field of sterilization. The sterilization method of the ultraviolet sterilization container is to use the light-emitting device to radiate ultraviolet light to the article storage cavity, and the ultraviolet light directly irradiates a sterilized article to kill the bacteria on the surface of the sterilized article to achieve the purpose of sterilization. At present, such ultraviolet sterilization containers can kill most bacteria on the surface of a sterilized article, but the sterilization effect is not satisfactory, especially for container-like sterilized articles. In addition, some portable UV sterilization containers are provided with a heating air duct, which can release hot air to the article storage cavity and dry the water stains remaining on the sterilized article, but the drying process consumes high energy.

The inventors of the present invention have found through experiments and studies that if the container mouth of the container-like sterilized article is aligned with the illumination direction, the sterilization effect is remarkably improved, and the desired sterilization effect can be achieved. However, the illumination device of the existing ultraviolet sterilization container is usually disposed on the upper wall of the article storage cavity, so that the sterilized article needs to be placed upright in the article storage cavity. For the portable ultraviolet sterilization container, for convenient carrying, the volume will be designed to be small. For some slender containers, such as bottles, cups, etc., it may not be possible to stand upright in the storage compartment of the article, and the stability of the upright placement is poor. The sterilized article, especially in the specified manner, adds unnecessary operations to the user, which may cause a bad feeling for the user.

SUMMARY

It is an object of the present invention to provide a portable UV sterilization container for improved sterilization, user convenience, and reduced energy consumption.

In order to achieve the above object, the technical solution adopted by the present invention is as follows.

Provided is a portable ultraviolet sterilization container, comprising a sterilization container body, the sterilization container body having an article storage cavity and a cover; wherein the sterilization container body is further provided with an illumination device, a heating air duct and a control system; wherein the control system is electrically connected to the illumination device and the heating air duct to control the illumination device and the heating air duct to release ultraviolet light and hot air to the article storage cavity, and wherein the illumination device comprises a plurality of illumination devices, and the plurality of illumination devices are fixed to a plurality of cavity walls of the article storage cavity; and the heating air duct is an inner circulation type heating air duct from the article storage cavity, through the interior of the cavity wall of the article storage cavity, and to the article storage cavity.

Preferably, the illumination device further comprises at least one light-reflecting device, wherein the light-reflecting device is fixed to a cavity wall of the article storage cavity for reflecting the ultraviolet light emitted by the illumination device.

Preferably, the portable ultraviolet sterilization container comprises five light-emitting devices and two light-reflecting devices, wherein the five light-emitting devices are respectively fixed to the top wall and the four side walls of the article storage cavity and the two light-reflecting devices are respectively fixed to the top wall and the bottom wall of the article storage cavity.

Preferably, the light-emitting device comprises a plurality of LEDs, and the plurality of the LEDs are arranged in array on a substrate, wherein the LED comprises a first LED chip having a wavelength of 260-280 nm and a second LED chip having a wavelength of 390-400 nm.

Preferably, an air outlet and a return air outlet of the heating air duct are disposed in adjacent cavity walls of the article storage cavity.

Preferably, the heating air duct has two air return outlets, and the two air return outlets are disposed on opposite cavity walls of the article storage cavity.

Preferably, an electric heating element of the heating air duct comprises a resistance wire and a frame having a sheet shape and a hollow portion; wherein the resistance wire is wound around the frame and a mesh structure is formed in the hollow portion.

Preferably, the control system comprises a main control board and a human machine interface, and the human machine interface comprises a first function key for outputting a first instruction of sterilizing and deodorizing to the main control board; a second function key for outputting a second instruction of sequentially sterilizing, deodorizing, drying, and thermostatically aseptic storage to the main control board; a third function key for outputting a third instruction of sterilizing, deodorizing and then drying to the main control board; and a fourth function key for outputting a fourth instruction of turning on or off the power to the main control board.

Preferably, in a constant temperature aseptic storage process, the illumination device and the heating air duct of the sterilization container are controlled to run in a low-power operation, and the constant temperature during the constant temperature aseptic storage is defined as when the sterilized article stored at the constant temperature is in contact with the human body, the human body feels warm and not uncomfortable.

Preferably, the sterilization container body is further provided with a battery.

Compared with the prior art, the present invention has at least the following beneficial effects.

Since the plurality of light-emitting devices are provided and the plurality of light-emitting devices are disposed on the plurality of cavity walls of the article storage cavity, the ultraviolet light can be radiated from the plurality of directions to the article storage cavity, and therefore, the sterilized article is not required to be placed in a specified manner to improve the sterilization effect and achieve effective sterilization, which is greatly convenient for the user.

Due to the use of the inner circulation heating air duct, ambient air is not introduced during the drying and constant temperature aseptic storage processes, and only a small amount of heat can heat the circulating air to the required temperature, thereby effectively reducing energy consumption.

Figure 1:
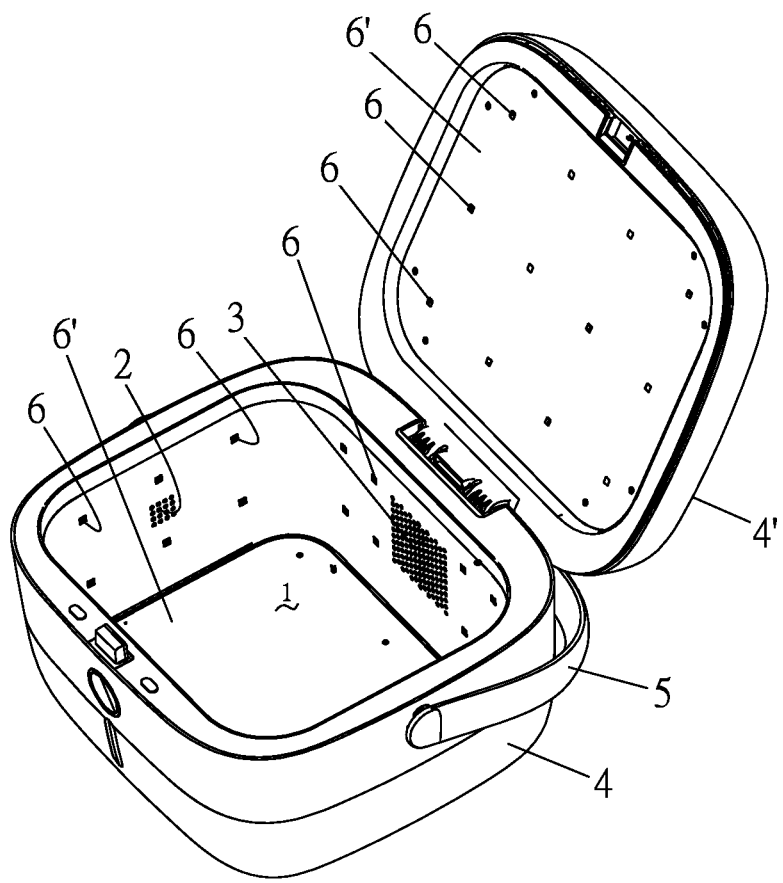
FIG. 1 is a schematic view showing the structure of the portable ultraviolet sterilization container.

Reference numerals: 1, article storage cavity; 2, return air outlet; 3, air outlet; 4, sterilization container body; 4', cover; 5, handle; 6, LED; 7, air duct; 7', fan; 8, electric heating elements; 9, frame; 10, resistance wire; 11, hollow portion; 12, first function key; 13, second function key; 14, third function key; 15, fourth function key.

DESCRIPTION OF THE EXEMPLARY EMBODIMENTS

The invention will be further described below in conjunction with the drawings and embodiments.

Referring to FIG. 1, the portable ultraviolet sterilization container includes a sterilization container body 4 having an article storage cavity 1, a cover 4' and a handle 5.

The sterilization container body 4 is also provided with an illumination device. The illumination device includes five light-emitting devices, and the five light-emitting devices are respectively fixed to the top wall and the four side walls of the article storage cavity 1. Each of the light-emitting devices includes a plurality of LEDs 6, and the plurality of the LEDs 6 are arranged in array on one substrate, thus constituting a surface light source for uniformly radiating ultraviolet light to the entire space of the article storage cavity 1. The LED 6 includes a first LED chip having a wavelength of 260-280 nm and a second LED chip having a wavelength of 390-400 nm, so that the LED generates ultraviolet light of two wavelengths, thereby achieving better sterilization effect. Moreover, the light radiated by the second LED chip is visible to the naked eyes, so that the light can pass through the observation window on the sterilization container body 4, and the user can intuitively understand the state of the sterilization work, for example, whether it is being sterilized, whether it is kept in a constant temperature and aseptic state.

The illumination device further comprises two reflecting devices 6', wherein the two light-reflecting devices 6' are respectively fixed on the top wall and the bottom wall of the article storage cavity 1. When working, the two light-reflecting devices 6' reflect repeatedly the ultraviolet light radiated by the light-emitting device on the top of the article storage cavity 1. On the one hand, the utilization of the ultraviolet light can be improved, and on the other hand, radiating ultraviolet light into the article storage cavity 1 at the upper, lower left, right, front, and rear directions is realized without installing the light-emitting device on the bottom wall of the article storage cavity 1. The light-reflecting device 6' may be made of a stainless steel plate or other metal plates, and preferably the reflecting surface is mirrored, and the light-reflecting device may also be a reflective coating disposed on the corresponding cavity wall of the article storage cavity 1, such as an aluminum coating, mercury coating, etc.

The sterilization container body 4 is also provided with a heating air duct. The heating air duct is an inner circulation type heating air duct from the article storage cavity 1, the inside of the cavity wall of the article storage cavity 1, and the article storage cavity 1.

Figure 2:
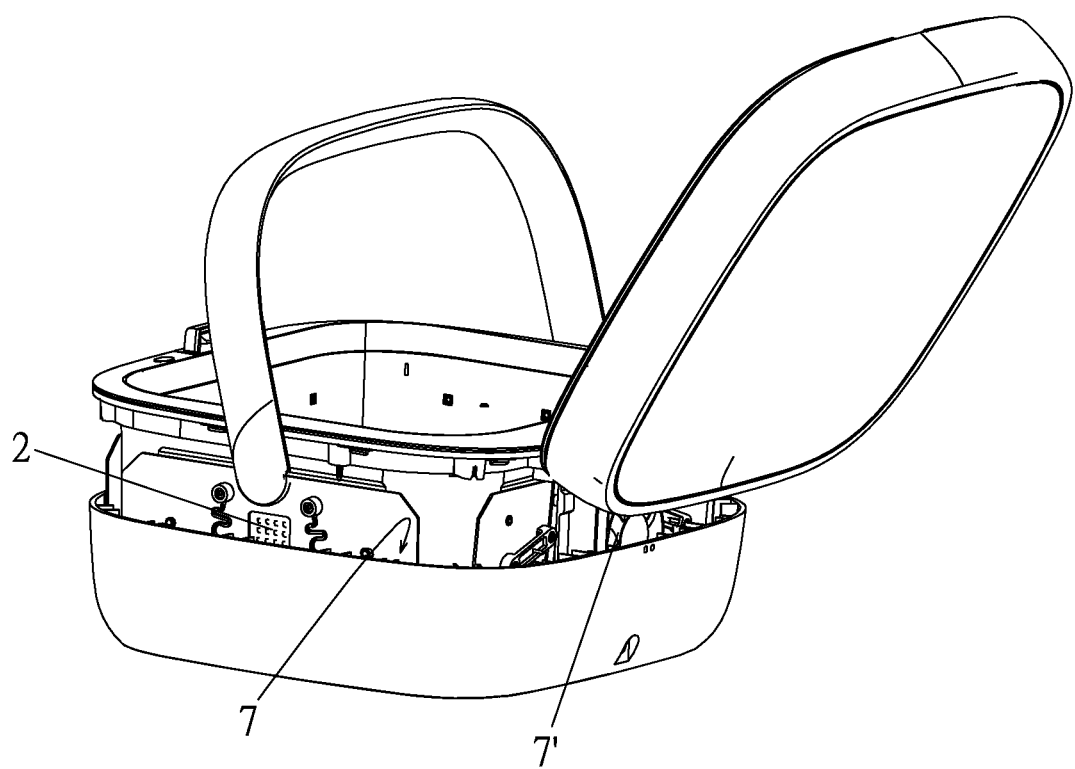
FIG. 2 is a schematic view of the positions of the air duct, the fan, and the return air outlet.

Referring to FIG. 1 and FIG. 2, the inner circulation type heating air duct specifically includes: a return air outlet 2 and an air outlet 3 which are opened in the cavity wall of the article storage cavity 1; an air duct 7 disposed in the interior of the cavity wall of the article storage cavity 1 and in communication with the air outlet 3 and the return air outlet 1; and a fan 7' and an electric heating element mounted in the air duct 7. During the heating operation, the fan 7' sucks the air in the article storage cavity 1 from the air return outlet 2 into the air duct 7, passes through the electric heating element, and then returns from the air outlet 3 to the article storage cavity 1, and circulates continuously in this manner. The article storage cavity 1 releases hot air to dry the article to be sterilized.

Since the circulating air is hot air and no ambient air is introduced, only a small amount of heat can heat the circulating air to a desired temperature, thereby effectively reducing energy consumption.

Referring to FIG. 1, the air outlet 3 and the return air outlet 2 of the heating air duct are respectively disposed on the adjacent cavity wall of the article storage cavity 1. When the fan 7' is in operation, a negative pressure is generated at the return air outlet 2, and this negative pressure acts on the air in the article storage cavity 1, which promotes the air diffusion. Compared with the air outlet 3 and the return air outlet 2 being disposed on the same side and the opposite sides, the positional design adopted in this embodiment can better diffuse the air entering the article storage cavity 1 from the air outlet 3.

Further, the heating air duct has two air return outlets 2, and the two air return outlets 2 are disposed on opposite cavity walls of the article storage cavity 1. Compared with the air return outlet 2 disposed only on one side, the design of the air return outlet on each of the opposite side walls makes the air diffusion effect in the article storage cavity 1 better.

Figure 3:
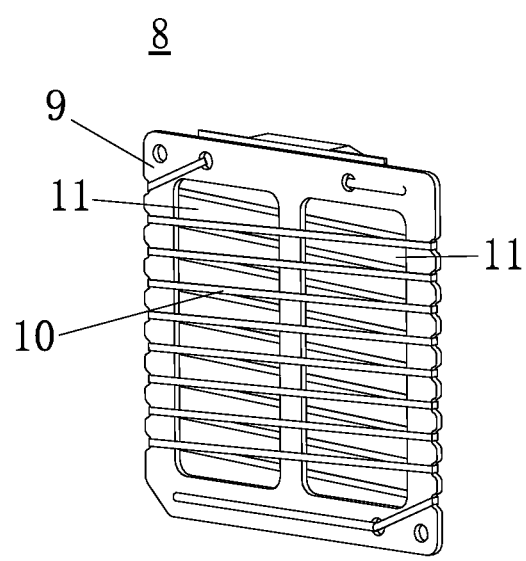
FIG. 3 is a schematic structural view of the electric heating element.

Referring to FIG. 3, the electric heating element 8 of the heating air duct comprises a resistance wire 10 and a frame 9 having a sheet shape and a hollow portion 11; wherein the resistance wire 10 is wound around the frame 9 and a mesh structure is formed in the hollow portion 11. With such an electric heating element 8, it can be easily fixed to the end of the fan 7', and the electric heating element 8 can be mounted very conveniently. Moreover, air can pass through the mesh structure, which can effectively increase the contact area of the air and the electric heating element, achieving rapid and efficient heating of the flowing air.

The sterilization container body 4 is further provided with a control system including a main control board and a human machine interface, and the control system is electrically connected with the illumination device and the heating air duct for controlling the illumination device to release ultraviolet light to the article storage cavity 1, and controls the heating air duct to release hot air to the article storage cavity 1.

Figure 4:
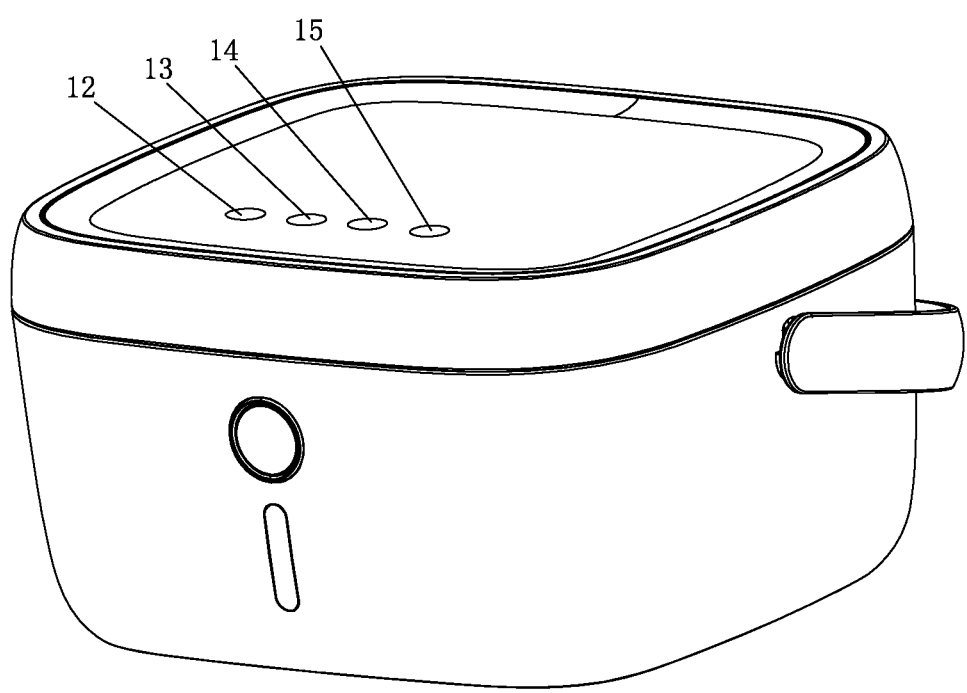
FIG. 4 is a schematic diagram of the human machine interface.

Referring to FIG. 4, the human machine interface includes a first function key 12, a second function key 13, a third function key 14, and a fourth function key 15, wherein the first function key 12 is configured to output a first instruction of sterilizing and deodorizing to the main control board, the second function key 13 is configured to output a second instruction of sequentially sterilizing, deodorizing, drying, and thermostatically aseptic storage to the main control board, the third function key 14 is configured to output a third instruction of sterilizing, deodorizing and then drying to the main control board, and a fourth function key 15 is configured to output a fourth instruction of turning on or off the power to the main control board.

When the first function key 12 is pressed, the main control board controls the operation of the illumination device to release ultraviolet light to the article storage cavity 1, to perform sterilization and deodorization, and to turn off the power after the task is finished. When the second function key 13 is pressed, the main control board first controls the illumination device to release ultraviolet light to the article storage cavity 1 to perform sterilization and deodorization; when the sterilization time is reached, the air duct structure is activated to release hot air to and then dry the article storage cavity. 1; after drying, the illumination device and the air duct structure are controlled to run in a low-power operation and continuously release a small amount of ultraviolet light and a small amount of hot air to the article storage cavity 1 to achieve constant temperature sterilization preservation. When the third function key 14 is pressed, the main control board first controls the illumination device to release ultraviolet light to the article storage cavity 1 to perform sterilization and deodorization; when the sterilization time is reached, the air duct structure is activated to release the hot air to and then dry the article storage cavity 1, and to turn off the power after the task is finished. In the power-on state, when pressing the fourth function key 15, the main control board controls the power to be turned off. In the power-off state, after pressing the fourth function key 15, the main control board controls the power to be turned on.

It can be seen that through the above four function keys, it is possible to select separate sterilization and deodorization, one-button sterilization to deodorization and dry, one-button sterilization to deodorization and dry and constant temperature aseptic storage, which can meet different sterilization needs of users, and various sterilization modes are one-button control, which is very convenient to use.

Further, the constant temperature during the constant temperature aseptic storage is defined as when the sterilized article stored at the constant temperature is in contact with the human body, the human body feels warm and not uncomfortable. Thus, on the one hand, when the user uses the sterilized article, it is known whether the sterilized article is sterilized by contacting the sterilized article. On the other hand, no matter when the sterilized article is taken out, the sterilized article has a warm feeling and can give the user a comfortable experience, and especially in a cold environment, and the comfortable experience is more remarkable.

In some embodiments, the sterilization container body is also provided with a battery that can be used when there is no power source, such as a picnic.

The present invention has been described in detail with reference to the preferred embodiments thereof, and the detailed description is not to be construed as limiting the scope of the invention. Various refinements, equivalent transformations, and the like performed by the above-described embodiments under the present invention should be included in the scope of the present invention.

What is claimed is:

1. A portable ultraviolet sterilization container, comprising a sterilization container body, the sterilization container body having an article storage cavity and a cover; wherein the sterilization container body is further provided with an illumination device, a heating air duct and a control system;

wherein the control system is electrically connected to the illumination device and the heating air duct to control the illumination device and the heating air duct to release ultraviolet light and hot air to the article storage cavity, and wherein the illumination device comprises a plurality of illumination devices, and the plurality of illumination devices are fixed to a plurality of cavity walls of the article storage cavity; and the heating air duct is an inner circulation type heating air duct from the article storage cavity, through the interior of the cavity wall of the article storage cavity, to the article storage cavity;

wherein an electric heating element of the heating air duct comprises a resistance wire and a frame having a sheet shape and a hollow portion; and wherein the resistance wire is wound around the frame and a mesh structure is formed in the hollow portion.

2. The portable ultraviolet sterilization container according to claim 1, wherein the illumination device further comprises at least one light-reflecting device, wherein the light-reflecting device is fixed to a cavity wall of the article storage cavity for reflecting the ultraviolet light emitted by the illumination device.

3. The portable ultraviolet sterilization container according to claim 2, comprising five light-emitting devices and two light-reflecting devices, wherein the five light-emitting devices are respectively fixed to a top wall and four side walls of the article storage cavity and the two light-reflecting devices are respectively fixed to the top wall and a bottom wall of the article storage cavity.

4. The portable ultraviolet sterilization container according to claim 1, wherein the light-emitting device comprises a plurality of LEDs, and the plurality of the LEDs are arranged in array on a substrate, wherein the plurality of the LEDs comprises a first LED chip having a wavelength of 260-280 nm and a second LED chip having a wavelength of 390-400 nm.

5. The portable ultraviolet sterilization container according to claim 1, wherein an air outlet and a return air outlet of the heating air duct are disposed in adjacent cavity walls of the article storage cavity.

6. The portable ultraviolet sterilization container according to claim 5, wherein the heating air duct has two air return outlets, and the two air return outlets are disposed on opposite cavity walls of the article storage cavity.

7. The portable ultraviolet sterilization container according to claim 1, wherein the control system comprises a main control board and a human machine interface, and the human machine interface comprises:

a first function key configured to output a first instruction of sterilizing and deodorizing to the main control board;

a second function key configured to output a second instruction of sequentially sterilizing, deodorizing, drying, and thermostatically aseptic storage to the main control board;

a third function key configured to output a third instruction of sterilizing, deodorizing and then drying to the main control board; and a fourth function key configured to output a fourth instruction of turning on or off the power to the main control board.

8. The portable ultraviolet sterilization container according to claim 7, wherein in a constant temperature aseptic storage process, the illumination device and the heating air duct of the sterilization container are controlled to run in a low-power operation, and the constant temperature during the constant temperature aseptic storage process is defined as when the sterilized article stored at the constant temperature is in contact with the human body, the human body feels warm and not uncomfortable.

9. The portable ultraviolet sterilization container according to claim 1, wherein the sterilization container body is further provided with a battery.

\* \* \* \* \*